United States Patent [19]

Reining

[11] Patent Number: 5,505,209
[45] Date of Patent: Apr. 9, 1996

[54] IMPEDANCE CARDIOGRAPH APPARATUS AND METHOD

[75] Inventor: William N. Reining, Cross Plains, Wis.

[73] Assignee: Reining International, Ltd., Madison, Wis.

[21] Appl. No.: 271,689

[22] Filed: Jul. 7, 1994

[51] Int. Cl.$^6$ ...................................................... A61B 5/00
[52] U.S. Cl. ............................ 128/734; 128/668; 128/713
[58] Field of Search ....................................... 128/668, 693, 128/713, 734

[56] References Cited

U.S. PATENT DOCUMENTS

| | | | |
|---|---|---|---|
| 3,340,867 | 9/1967 | Kubicek et al. | |
| 4,450,527 | 5/1984 | Sramek | 364/415 |
| 4,676,253 | 6/1987 | Newman et al. | 128/693 |
| 4,807,638 | 2/1989 | Sramek | 128/672 |
| 5,178,154 | 1/1993 | Ackmann et al. | 128/713 |
| 5,265,615 | 11/1993 | Frank et al. | 128/672 |
| 5,309,917 | 5/1994 | Wang et al. | 128/713 |
| 5,316,004 | 5/1994 | Chesney et al. | 128/713 |

OTHER PUBLICATIONS

*Uber ein neues Verfahren zur Darstellung der Herztatigkeit (Dielektrographie)*, by Edgar Atzler et al. German article with attached summary and translation.

*Protecting Medical Devices from Radio–Frequency Interference*, by William D. Kimmel et al., Medical Device & Diagnostic Industry, Circle Reader Service #52, pp. 68–78.

*Cardiac Output by Electrical Impedance*, by B. Bo Sramek, Apr. 1982.

*Development and Evaluation of an Impedance Cardiac Output System*, by W. G. Kubicek, Ph.D. et al., Aerospace Medicine, Dec. 1966.

Primary Examiner—Angela D. Sykes
Assistant Examiner—Robert L. Nasser, Jr.
Attorney, Agent, or Firm—Quarles & Brady

[57] ABSTRACT

An impedance cardiograph which determines cardiac output from a measurement of variations of chest impedance, provides an improved method of calculating the effect of patient volume on the measurement from measurable patient height and chest circumference, and provides a correction process that identifies as a source of error variations in the first derivative of impedance. This latter source of error is minimized by preprocessing the impedance derivative value with a compression function which reduces the range of values of the impedance derivative when that value differs significantly from a norm of the population.

16 Claims, 2 Drawing Sheets

IMPEDANCE CARDIOGRAPH APPARATUS AND METHOD

FIELD OF THE INVENTION

The present invention relates to impedance cardiographs which determine cardiac output by evaluating changes in impedance across the patient's chest cavity.

BACKGROUND OF THE INVENTION

Impedance cardiography is a non-invasive technique for determining cardiac performance in humans. When such equipment is employed, a high frequency electric signal is applied to the patient across outer electrodes positioned, for example, on the patient's head and lower thorax. Voltage differences between sensing inner electrodes positioned between the outer electrodes on the patient's neck and chest are measured and used to compute an impedance (Z). The impedance is based on the low magnitude, known electrical current passing between the outer electrodes.

In 1932, Atzler and Leyman reported that cardiac output of a human could be determined by such impedance methods in *Uber ein neues Verfahren zur Darstellung der Herztatigkeit (Dielektrographie)*, Arbeitsphysiologie, 5:636–680. In 1966, Kubichek reported the ability to correlate changes in base line impedance and the first derivative of impedance to stroke volume (SV) according to the following Equation (1) disclosed in U.S. Pat. No. 3,340,867 and in the publication: *Development and Evaluation of an Impedance Cardiac Output System*, Aerospace Medicine, 37: 1208–1212.

$$SV = \frac{\rho * L^2 * \frac{d\hat{Z}}{dt} * L_{vet}}{Z_0^2} \quad (1)$$

where: p1 $\rho$ is the resistivity of blood;

L is the spacing between the sensing electrodes;

$Z_0$ is an average or baseline impedance; and $$\frac{d\hat{Z}}{dt}$$

is the magnitude of the peak negative value of the time derivative of the impedance Z for a period of time, typically a second.

Cardiac output may be deduced from stroke volume by multiplying the latter times the heart rate.

Although the Kubichek formula provides a value that correlated with cardiac output, the absolute accuracy of the method remained doubtful and, in particular, subjects with certain cardiovascular problems show values with great inaccuracies.

In 1982, Sramek proposed a modification of the Kubichek formula of equation (1) which resolved the base line impedance $Z_0^2$ into a dynamic and static component as reported in the publication: *Cardiac Output by Electrical Impedance*, Med. Elect., 2:274–290. The static term $Z_0s$ was described by the following equation:

$$Z_0s = \frac{\rho * L}{A} \quad (2)$$

where A is the area of the thorax being measured.

The dynamic component $Z_0d$ was simply the baseline or average of the impedance being measured:

$$Z_0d = Z_0 \quad (3)$$

Incorporating the static term and dynamic term into the Kubichek equation provides the following formula:

$$SV = \frac{A * L * \frac{d\hat{Z}}{dt} * L_{vet}}{Z_0} \quad (4)$$

The value of A may be estimated by approximating the chest as a cylinder in which case equation (4) becomes:

$$SV = \frac{C^2 * L * \frac{d\hat{Z}}{dt} * L_{vet}}{4 * \pi * Z_0} \quad (5)$$

where C is circumference of the chest near the area of measurement. Alternatively, Sramek proposed that the term $$\frac{C^2 * L}{4 * \pi}$$

be replaced with either $$\frac{L^3}{4.25}, \text{ or } \frac{(1.7*H)^3}{4.25}$$

where H is the height of the patient because 1.7*H approximates L.

These approximations did not produce good results and so Sramek was ultimately led to produce a set of charts attempting to establish correlation between area and the three factors of gender, height and weight.

In 1986, Bernstein proposed a modified equation in which the separation of the electrodes and the height of the patient were considered, in the following form:

$$SV = \frac{\left(\frac{L + 1.5*H}{2}\right)^3 * \frac{d\hat{Z}}{dt} * L_{vet}}{4.25 * Z_0} \quad (6)$$

All of the above methods suffer from lack of accuracy and indicate, in some subjects, falsely high or low values of stroke volume.

SUMMARY OF THE INVENTION

The present invention provides an improved method and apparatus for deducing stroke volume (and hence cardiac output) from impedance measurements. The invention provides an improved estimation of body volume and a processing of the derivative of the impedance signal that improves the reliability of the derived values of stroke volume and cardiac output.

Specifically, in an impedance cardiograph for use on a human patient having a height of H and a chest circumference C, a means for applying an electrical excitation signal to the patient is used in conjunction with electrodes positioned on the chest with a separation distance of L, the electrodes producing a first electrical impedance signal Z which varies with impedance changes in the patient. A user input device, such as a keyboard, is provided to enter data on the height, electrode separation distance and circumference to produce corresponding second and third electrical signals H, L and C indicating those values. An electrical circuit, which may be an electronic computer, receives the second and third electrical signal and provides an indication of the patient's cardiac stroke volume, SV, as a function of Z, A, L and left ventricular ejection interval $L_{vet}$ where A is deduced by the following approximation:

$$A = \frac{L}{K*H*C}$$

where K is a predetermined constant.

Thus, the impedance cardiograph may calculate SV according to the following formula:

$$SV = \frac{L}{K*H*C} \frac{\rho*C^2*L*L_{vet}}{4*\pi*Z_0} \frac{d\hat{Z}}{dt}$$

which may be simplified to:

$$SV = \frac{\rho*C*L^2*L_{vet}}{4*K*H*\pi*Z_0} \frac{d\hat{Z'}}{dt}$$

or by combining constants:

$$SV = \frac{\rho*C*L^2*L_{vet}}{K*H*Z_0} \frac{d\hat{Z'}}{dt}$$

Thus, it is one object of the invention to provide a simple, yet more accurate characterization of a critical term A used in the calculation of stroke volume from patient impedance. In the present invention, the area of the impedance measurement, which is difficult to measure, is accurately derived from the readily measured values of chest circumference and patient height.

The present invention has also recognized that variation in the derivative of impedance, one of the factors used in deducing stroke volume, is a significant source of inaccuracy in the computed stroke volume. Accordingly, whereas $$\frac{d\hat{Z}}{dt}$$

may simply be the magnitude of the minimum derivative of impedance with time, it may also be compressed to reduce the amount that this maximum deviates from the norm. One method of weighting the maximum is according to the formula:

$$\frac{d\hat{Z}}{dt} = \frac{d\hat{Z}n}{dt} = \frac{\frac{d\hat{Z}}{dt}}{\sqrt{\frac{d\hat{Z}}{dt} / \frac{\overline{dZ}}{dt}}}$$

where:

$$\frac{d\hat{Z}}{dt}$$

is the magnitude of the minimum time derivative of $$\frac{d\hat{Z}n}{dt}$$

is the compressed value of $$\frac{d\hat{Z}}{dt};$$

$$\frac{\overline{dZ}}{dt}$$

is a predetermined normal value and is an average value of $$\frac{d\hat{Z}}{dt}$$

for a population.

Thus, it is yet another object of the invention to reduce the effect of a significant source of error in the calculation of stroke volume from impedance by implementation of a normal based weighting system.

The foregoing and other objects and advantages of the invention will appear from the following description. In the description, reference is made to the accompanying drawings which form a part hereof and in which there is shown by way of illustration, a preferred embodiment of the invention. Such embodiment does not necessarily represent the full scope of the invention, however, and reference must be made therefore to the claims herein for interpreting the scope of the invention.

DETAILED DESCRIPTION OF THE PREFERRED EMBODIMENT

Figure 1:
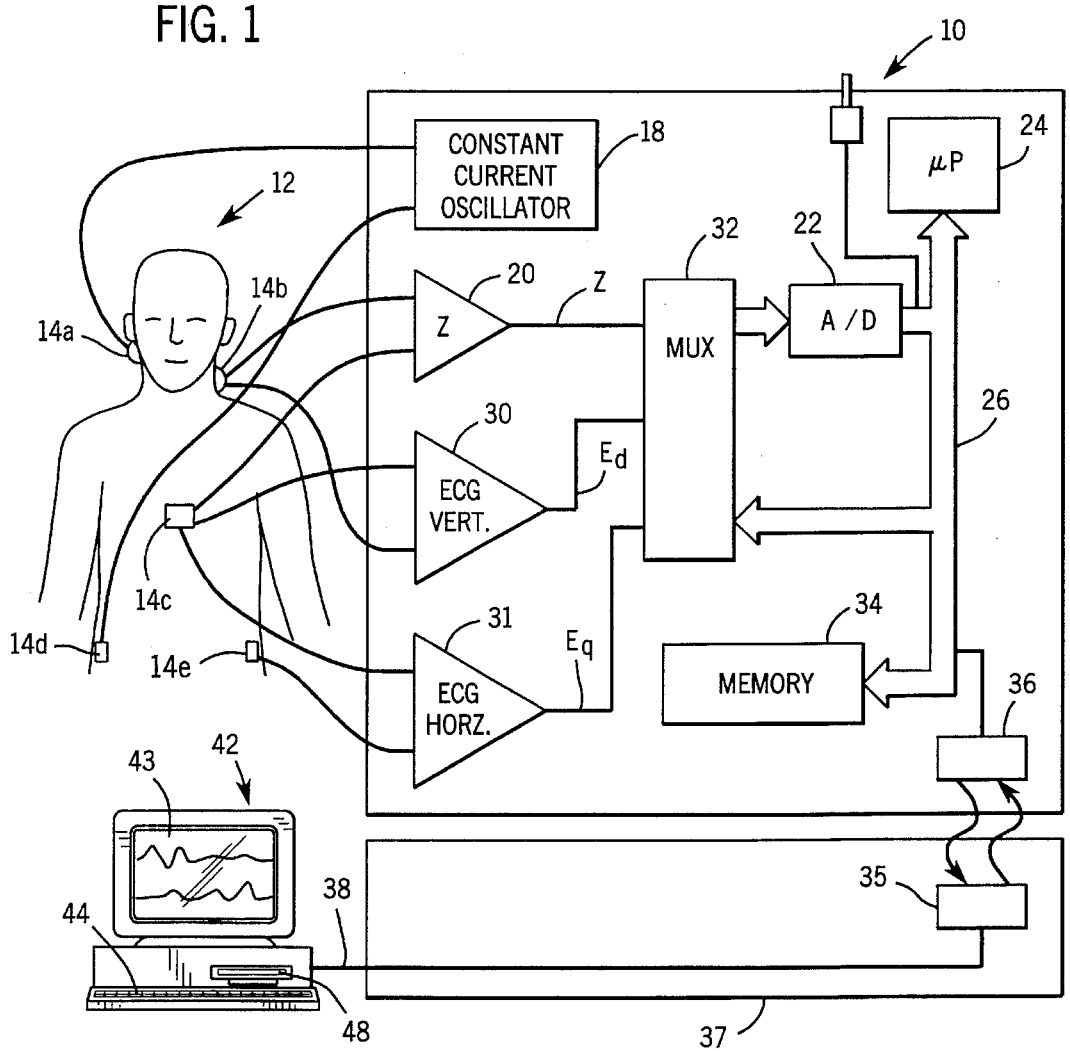
FIG. 1 is a block diagram of the circuitry for an impedance cardiograph according to the present invention, showing a computer as used to analyze the impedance data to produce a value of stroke volume and cardiac output.

Referring to FIG. 1, a portable impedance cardiograph 10 is connected to a patient 12 by five patch electrodes 14(a)–(e). The first electrode 14(a) may be positioned on the patient's skin behind the right ear at the level of the ear canal. The second electrode 14(b) may be located at the left side of the neck on a flat surface approximately between the level of the chin and base of the hairline at least 5 cm below the level of electrode 14(a). The third electrode 14(c) may be located just above the base of the sternum on the anterior median lines. The fourth and fifth electrodes 14(d) and 14(e) may be located at least 5 cm below the electrode 14(c) on the patient's right and left sides respectively at the costal arch and the anterior axillary line.

Electrodes 14(a) and (d) are attached to an oscillator 18 which produces a constant current of approximately 1 milliamperes RMS through the patient 12. This electrical excitation establishes a series of equal potential surfaces through the patient 12 perpendicular to a line extending between the two outer electrodes 14(a) and 14(d).

Electrodes 14(b) and 14(c) may sense the equal potential lines generated by the current flowing between the outer electrodes 14(a) and 14(d). Because the current between the outer electrodes 14(a) and 14(d) is of constant amplitude, the amplitude of the voltage sensed between the inner electrodes 14(b) and 14(c) is proportional to the thoracic impedance of the patient 12. The inner electrodes 14(b) and 14(c) are connected to differential amplifier 20 producing a signal Z.

The amplifier 20 includes isolation circuitry that electrically isolates the inner electrodes 14(b) and 14(c) from the subsequent circuitry. Differential amplifier 20 also includes a precision half wave rectifier and low pass filter so as to provide a slowly varying DC signal whose value is proportional to the impedance being measured. The input impedance of the differential amplifier 20 is very high (e.g. 10 megohms) as compared to the impedance of the patient 12 between the inner electrodes 14(b) and 14(c). Thus, negligible current will flow through the inner electrodes 14(b) and 14(c) to amplifier 20.

The impedance signal Z is received by a multiplexer 32, such as are known in the art, to be periodically connected to an analog to digital converter 22 which samples the signal and provides a binary data word that may be read by microprocessor 24 via a bus 26.

A first, vertical ECG signal is measured across electrodes 14(b) and 14(c) lying generally along a generally vertical line. This ECG signal is received by differential amplifier 30 to produce an electrocardiograph signal $E_v$ according to techniques well known in the art.

A second, horizontal ECG signal is measured across electrodes 14(c) and 14(e) lying generally along a horizontal line. This ECG signal is received by differential amplifier 31 to produce an electrocardiograph signal $E_h$. Both signals $E_v$ and $E_h$ are received by multiplexer 32 which periodically connects these signals to the analog to digital converter 22 to be sampled and converted to digital words for transmission on internal bus 26.

Differential amplifiers 30 and 31 receiving the ECG signal also include isolation circuitry and a low pass filter having a cut-off frequency such as to substantially remove the 50 kHz oscillator signal from oscillator 18. As will be described further below, the direct and quadrature ECG signals are combined to produce a single ECG signal largely independent of the electrical orientation of the patient's heart.

Also attached to bus 26 is computer memory 34 which may be composed of both random access memory ("RAM") and read only memory ("ROM") according to well known computer architectures. Memory 34 provides a means for storage of the binary representations of signals Z and $E_v$ and $E_h$ under the control of microprocessor 24, and also holds a stored program defining the operation of the microprocessor 24 for the calculation of cardiac output as will be described.

Also attached to bus 26 is a pushbutton switch 25 which may be used by the patient to mark the occurrence of some event, such as a cardiac episode, during the recording of data from the patient 12 as will be described.

The bus 26 also communicates with an infra-red transceiver 36, which permits the microprocessor to transmit and receive data to and from a similar transceiver 35 in a detachable base unit 37. The transceiver 35 is connected by a serial cable 38 to a desk-top computer 42 having a video monitor 43, a keyboard 44 and a disk drive 48 such as are known in the art. As such the impedance cardiograph 10 is portable and may be powered by internal batteries so as to be carried with the patient in the manner of a Holter monitor.

Generally, the impedance cardiograph receives signals from the patient 12, isolates, amplifies and filters those signals, and then translates the signals to digital values which may be read and stored by microprocessor 24 to be processed according to the stored program in memory 34. Results of the processing may be transmitted to the computer 42 to be displayed on the video monitor 43 or saved on disk 48.

The operation of the impedance cardiograph 10 according to the stored program is controlled by a human operator through keyboard 44. The operator prepares the patient 12 for the impedance measurements and may enter certain data to the keyboard 44 that characterizes the patient 12 and that is necessary for the analysis of the signals from the patients 12 as will be described. This analyses is done in partially in the microprocessor 24 so as to reduce the amount of data to be stored in memory 34, but, as will be understood in the art, the analyses of the data may be shared between the microprocessor 24 and the computer 42 as a matter of engineering choice.

Figure 2:
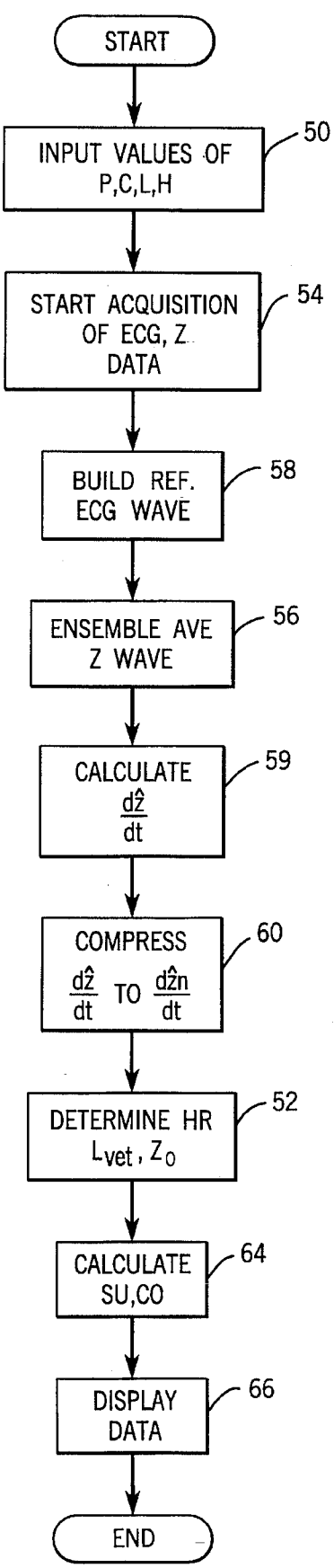
FIG. 2 is a flow chart of the software employed by the computer of FIG. 1 in analyzing the impedance and ECG signals acquired from the patient.

Referring now to FIG. 2, at the first step in the analyses, indicated by process block 50, certain data related to the particular patient 12 or related to fundamental and essentially universal physiological parameters, may be entered by the operator.

The first of these parameters is ρ which is the resistivity of blood in ohms-cm. Generally, this value may be approximated as a constant for all patients, however, it may be modified by the operator in abnormal cases based on the measurement of hematacrit.

A second value, C, is the circumference of the patient's chest in cm taken at the site of inner electrode 14(c) around the patient's chest.

The value L is also input, being the distance between the inner electrodes 14(b) and 14(c) in cm. The height of the patient, H, in cm is also entered.

Once the necessary fixed parameters are entered at process block 50, two variable parameters: heart rate HR and ventricular ejection time $L_{vet}$ are entered per process block 52. For this purpose, the ECG signal E may be directly displayed on the video monitor 43 so that these quantities may be determined according to methods well known in the art. The ECG signal is calculated from the vector sum of the values of $E_v$ and $E_h$ most simply as follows:

$$ECG = \sqrt{E_v^2 + E_h^2}$$

This vector summing reduces the need to precisely orient the ECG electrodes with respect to an electrical polarity of the heart and therefore in practice provides a superior ECG signal.

Generally, $L_{vet}$ is the time between the opening of the aortic valve and the closing of the aortic valve. The heart rate is simply the number of beats per second which is the inverse of the period between successive R waves. The heart rate may be averaged over a number of beats according to methods well known in the art. Both quantities may be determined by inspection by the operator or preferably may be determined automatically after sufficient ECG and Z data is acquired as indicated by process block 52. The value of $L_{vet}$ in the preferred embodiment is determined by analyzing the impedance signal Z to measure a period beginning when $$\frac{dZ}{dt}$$

is first less than zero and ending when the value of $$\frac{dZ}{dt}$$

reaches a local maximum above zero. The heart rate HR is measured by detecting and counting R waves in the ECG signal.

The acquisition of the ECG and Z signal per process block 54 continues. This acquisition is on a continuous basis and occurs concurrently with the subsequent calculations so that the cardiac output may be continuously stored in memory 34 or displayed in essentially a real-time manner.

The acquired impedance data is in the form of discreet samples taken approximately 300 times per second, each sample which may be represented by $Z_i$ where i is an index number of the particular sample. As each sample $Z_i$ is acquired, it is stored in consecutive addresses in memory 34 to indicate its relative position with respect to other samples and to indicate the time of the sample indirectly through the constant sampling rate.

Because the impedance cardiograph 10 is portable, there is a risk that artifacts may be introduced into the impedance measurement by electrode movement. This is because the measured impedance values are approximately two orders of magnitude lower than the electrode to skin resistance. Accordingly, the impedance data over a period of approximately one minute is "ensemble" averaged, per process block 56, to reduce its noise content. Ensemble averaging is a well known technique in which blocks of impedance data are averaged on a point-by-point basis with other blocks of impedance data so that the averaged points are from corresponding portions of the impedance waveform cycle. Thus, the shape of the impedance waveform is not destroyed in the averaging process. In order to perform such ensemble averaging, it is necessary to identify a common fiducial point to align the blocks of data. Selection of the fiducial point must be extremely precise, otherwise the characteristics of the impedance waveform will be "blurred" by a mis-registration of other blocks.

This fiducial point may be the peak of the R wave of the ECG signal. Normal techniques for determining the time of the R wave, such as may be used for the measurement of heart rate, however, are not suitably accurate for the purpose of ensemble averaging. Accordingly an extremely accurate identification process is used. First, as represented by process block 58, the ECG signal is monitored to isolate a standard R wave. Only portions of the received ECG signal having no detectable artifacts or noise are considered. This standard R wave is then correlated to the incoming ECG signal to identify the precise location of the R wave (by the value of highest correlation). This location is used at the point of common alignment for the impedance waveforms to be ensemble averaged. Periodically, a new standard R wave is obtained so that the standard remains current over time.

After pairs of data $Z_i$ and $Z_i+1$ are acquired and averaged, a derivative value is $$\frac{dZ_i}{dt}$$

may be computed by a simple subtraction of adjacent samples of the ensemble average per process block 58, that is:

$$\frac{dZ_i}{dt} = Z_{i+1} - Z_i \quad (7)$$

Alternatively, in order to reduce the presence of 50 Hz or 60 Hz noise, this derivative computation can employ samples $Z_{i+6}-Z_i$ or $Z_{i+5}$, respectively.

It has been determined that variation in the magnitude of the minimum of this value, $$\frac{d\hat{Z}}{dt},$$

is a significant source of error in the calculation of cardiac output. Accordingly, at process block 60, a compressed derivative, $$\frac{d\hat{Z}n}{dt}$$

is computed according to the following formula:

$$\frac{d\hat{Z}n}{dt} = \frac{\frac{d\hat{Z}}{dt}}{\sqrt{\frac{d\hat{Z}}{dt} / \frac{\overline{dZ}}{dt}}} \quad (8)$$

where:

$$\frac{d\hat{Z}}{dt}$$

is the magnitude of the minimum time derivative of Z as previously defined;

$$\frac{d\hat{Z}n}{dt}$$

the compressed value of $$\frac{d\hat{Z}}{dt};$$

$$\frac{\overline{dZ}}{dt}$$

is the predetermined normal maximum value and is an average value $$\frac{d\hat{Z}}{dt}$$

for a population and is about 1.73 ohms per second.
Equation (8) has the effect of reducing the excursions of $$\frac{d\hat{Z}}{dt} \text{ from } \frac{\overline{dZ}}{dt}.$$

Other nonlinear compression systems may also be used provided they have the effect of compressing $$\frac{d\hat{Z}}{dt}$$

about the norm.

At succeeding process block 52, the value of $Z_0$ is also computed. $Z_0$ is the base transthoracic impedance and in this implementation, simply the average value of Z for one cardiac cycle. Because of the need to average a number of samples, when the sampling is first begun, no display is provided to the video terminal 43 until sufficient samples have been made to insure the accuracy of this value $Z_0$.

At process block 64 a stroke volume may be calculated according to the following formula:

$$SV = \frac{L}{K*H*C} \frac{\rho * C^2 * L * L_{vet}}{4*\pi*Z_0} \frac{d\hat{Z}}{dt} \quad (9)$$

It will be recognized that this is simply Equation (5) with the addition of a factor $\rho$ and the addition of a factor $$\frac{L}{K*H*C},$$

this latter factor approximating a slice of body volume in the area of the impedance measurement.

This calculation of stroke volume has shown significant improvements in accuracy and correlation coefficients in clinical studies.

Also at process block 64, cardiac output may be determined by multiplying the stroke volume times the heart rate:

$$CO = SV * HR \quad (10)$$

As cardiac output is computed, it is displayed in graphical form on video monitor 43. Thus, the operator is provided with concurrent ECG data and cardiac output data on an essentially real-time basis per the display indicated by process block 66.

After each updating of the display of 43 is accomplished, the program acquire additional data until the measurement session is complete.

While this invention has been described with reference to particular embodiments and examples, other modifications and variations will occur to those skilled in the art in view of the above teachings. Accordingly, the present invention is not limited to the preferred embodiment described herein, but is instead defined in the following claims.

I claim:

1. An impedance cardiograph used to evaluate cardiac output of a human patient having a height and a chest circumference and chest cross-sectional area A comprising:

means for applying an electrical excitation signal to the chest of a patient;

electrodes, adapted to be positioned on the patient with a separation distance of L thereby being responsive to the excitation signal, for producing a first electrical signal Z which varies with impedance changes in the patient;

an input device for receiving values of the height and circumference and providing corresponding second and third electrical signals H and C indicating those values;

electrical circuit means for receiving the first, second and third electrical signals and providing an indication of the patient's cardiac stroke volume SV as a function of Z, A, and L;

where A is deduced by the following approximation:

$$\frac{L}{K*H*C}$$

where K is a predetermined constant.

2. The impedance cardiograph of claim 1 wherein the electric circuit means calculates SV according to the following formula:

$$SV = \frac{L}{K*H*C} \cdot \frac{\rho * C^2 * L * L_{vet}}{4*\pi*Z_0} \cdot \frac{d\hat{Z}}{dt}$$

where $\rho$ is the resistivity of blood;

$Z_0$ is an average baseline impedance;

$L_{vet}$ is a left ventricular ejection interval; and $$\frac{d\hat{Z}}{dt}$$

is a function of the time derivative of the impedance Z.

3. The impedance cardiograph of claim 2 wherein $$\frac{d\hat{Z}}{dt}$$

is a magnitude of the minimum time derivative of Z.

4. The impedance cardiograph of claim 2 wherein $$\frac{d\hat{Z}}{dt}$$

is a compressed value of a time derivative of Z about a predetermined normal value so that $$\frac{d\hat{Z}}{dt}$$

has a value less than the time derivative of Z if the time derivative of Z is greater than said predetermined normal value and $$\frac{d\hat{Z}}{dt}$$

has a value greater than the time derivative of Z if the time derivative of Z is less than the predetermined normal value.

5. The impedance cardiograph of claim 1 wherein K is substantially 0.875.

6. An impedance cardiograph used to evaluate cardiac output of a human patient comprising:

means for applying an electrical excitation signal to the chest of a patient;

electrodes, adapted to be positioned on the patient for producing a first electrical signal Z which varies with impedance changes in the patient;

an electronic processor for calculating a time derivative of Z, and providing a non-linearly non-linearly compressed derivative, having a value less than the time derivative of Z if the time derivative of Z is greater than a predetermined normal value and having a value greater than the time derivative of Z if the time derivative of Z is less than the predetermined normal value;

electrical circuit means for providing an indication of patient's cardiac stroke volume SV as a function of the compressed time derivative.

7. The impedance cardiograph of claim 6 wherein the electronic processor produces the compressed value of the time derivative of Z according to the following formula:

$$\frac{d\hat{Z}n}{dt} = \frac{\frac{d\hat{Z}}{dt}}{\sqrt{\frac{d\hat{Z}}{dt} / \frac{\overline{dZ}}{dt}}}$$

where:

$$\frac{d\hat{Z}}{dt}$$

is a time derivative of Z $$\frac{d\hat{Z}n}{dt}$$

is the compressed time derivative of Z $$\frac{\overline{dZ}}{dt}$$

is the predetermined normal value and is an average value of $$\frac{d\hat{Z}}{dt}$$

for a population.

8. The impedance cardiograph of claim 6 wherein the predetermined normal value is substantially 1.73 ohms per second.

9. A method of evaluating the cardiac output of a human patient having a height H and a chest circumference C and chest cross-sectional area A comprising the step of:
 (a) applying an electrical excitation signal to the chest of a patient;
 (b) positioning electrodes on the patient with a separation distance of L thereby being responsive to the excitation signal to produce a first electrical signal Z which varies with impedance changes in the patient;
 (c) employing an electronic computer to:
  (i) receive values of the height and circumference and providing corresponding second and third electrical signals H and C indicating those values;
  (ii) evaluate the patient's cardiac stroke volume SV as a function of Z, A, L and left ventricular ejection interval $L_{vet}$;

where A is deduced by the following approximation:

$$\frac{L}{K*H*C}$$

in which K is a predetermined constant.

10. The method of claim 9 including calculating SV using said electronic computer according to the following formula:

$$SV = \frac{L}{K*H*C} \cdot \frac{\rho*C^{2}*L*L_{vet}}{4*\pi*Z_0} \cdot \frac{d\hat{Z}}{dt}$$

where
 $\rho$ is the resistivity of blood;
 $Z_0$ is an average baseline impedance; and $$\frac{d\hat{Z}}{dt}$$

is a function of the time derivative of the impedance Z.

11. The method of claim 10 wherein $$\frac{d\hat{Z}}{dt}$$

is a magnitude of the minimum time derivative of Z.

12. The method of claim 10 wherein $$\frac{d\hat{Z}}{dt}$$

is a compressed value of the time derivative of Z about a predetermined normal value so that $$\frac{d\hat{Z}}{dt}$$

has a value less than the time derivative of Z if the time derivative of Z is greater than said predetermined normal value and $$\frac{d\hat{Z}}{dt}$$

has a value greater than the time derivative of Z if the time derivative of Z is less than the predetermined normal value.

13. The method of claim 12 wherein K is substantially 0.875.

14. A method of evaluating cardiac output of a human patient comprising the steps of:
 (a) applying an electrical excitation signal to the chest of a patient;
 (b) positioning electrodes on the patient for producing a first electrical signal Z which varies with impedance changes in the patient;
 (c) determining a compressed derivative of the impedance signal Z, having a value less than the time derivative of Z if the time derivative of Z is greater than a predetermined normal value and having a value greater than the time derivative of Z if the time derivative of Z is less than the predetermined normal value; and
 (e) evaluating the patient's cardiac stroke volume SV as a function of the compressed time derivative.

15. The method of claim 14 step (c) is according to the following formula:

$$\frac{d\hat{Z}n}{dt} = \frac{\frac{d\hat{Z}}{dt}}{\sqrt{\frac{d\hat{Z}}{dt} / \frac{\overline{dZ}}{dt}}}$$

where:

$$\frac{d\hat{Z}}{dt}$$

is the magnitude of the minimum time derivative of Z $$\frac{d\hat{Z}n}{dt}$$

is the compressed time derivative of z $$\frac{\overline{dZ}}{dt}$$

is the predetermined normal value and is an average value of $$\frac{d\hat{Z}}{dt}$$

for a population.

16. The method of claim 14 wherein the predetermined normal value is substantially 1.73 ohms per second.

* * * * *

UNITED STATES PATENT AND TRADEMARK OFFICE
CERTIFICATE OF CORRECTION

PATENT NO. : 5,505,209
DATED : April 9, 1996
INVENTOR(S) : William N. Reining

It is certified that error appears in the above-indentified patent and that said Letters Patent is hereby corrected as shown below:

Col. 1, line 37     "where: p1 ρ is the" should be
--where:
ρ is the--

Col. 3, line 54     "derivative of " should be
--derivative of Z;--.

Signed and Sealed this

Twenty-third Day of July, 1996

Attest:

BRUCE LEHMAN

Attesting Officer     Commissioner of Patents and Trademarks